United States Patent
Bassarab et al.

(10) Patent No.: US 8,096,971 B2
(45) Date of Patent: Jan. 17, 2012

(54) DUAL CHAMBER CONTAINER FOR LYOPHILIZATION, PROCESS FOR THE FILLING UP AND USE THEREOF

(75) Inventors: Stefan Bassarab, Biberach (DE); Alexander Bauer, Biberach (DE); Nicole Denkinger, Biberach (DE); Patrick Garidel, Norderstedt (DE); Markus Hemminger, Biberach (DE); Hans-Joachim Kern, Mittelbiberach (DE); Andreas Langer, Maselheim (DE); Ingo Presser, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1252 days.

(21) Appl. No.: 11/464,494

(22) Filed: Aug. 14, 2006

(65) Prior Publication Data

US 2007/0060877 A1    Mar. 15, 2007

(30) Foreign Application Priority Data

Aug. 13, 2005  (DE) .......................... 10 2005 038 368

(51) Int. Cl.
*A61M 37/00* (2006.01)
(52) U.S. Cl. ........................................... 604/84; 604/89
(58) Field of Classification Search ............... 604/82–92
See application file for complete search history.

(56) References Cited

U.S. PATENT DOCUMENTS

| | | | |
|---|---|---|---|
| 1,961,023 A | | 5/1934 | West |
| 2,393,578 A | * | 1/1946 | Waite ............................ 215/248 |
| 3,025,991 A | | 5/1960 | Gillon |
| 3,326,215 A | | 6/1967 | Sarnoff et al. |
| 3,454,178 A | | 7/1969 | Bender et al. |
| 3,810,469 A | | 5/1974 | Hurschman |
| 4,036,225 A | | 7/1977 | Maury |
| 4,048,999 A | | 9/1977 | Kobel |
| 4,254,768 A | | 3/1981 | Ty |
| 4,479,578 A | | 10/1984 | Brignola et al. |
| 4,488,656 A | * | 12/1984 | Fukuoka et al. ............... 215/307 |

(Continued)

FOREIGN PATENT DOCUMENTS

AU    2003236878 A1    10/2003

(Continued)

OTHER PUBLICATIONS

Office Action for co-pending, related U.S. Appl. No. 11/464,493, Mar. 19, 2009.

(Continued)

*Primary Examiner* — Theodore Stigell
(74) *Attorney, Agent, or Firm* — Michael P. Morris; David L. Kershner (57) ABSTRACT

Double chamber container for holding and combining, e.g., a lyophilizate and a liquid reconstitution medium, comprising an integral cylindrical body (15) with a closure (20, 60) at each of the two ends (5, 70),
an upper movable closure (60) to the side of the reconstitution medium and a lower closure (20) to the side of the lyophilizate,
a separating stopper (40) that can be moved in the cylindrical body (15) as a seal between the upper chamber (50) and the lower chamber (30),
a bypass (35), arranged below the separating stopper (40), having a length L greater than the height H of the separating stopper (40),
wherein
at the lower end (5) in the wall of the cylindrical body (15) or in the lower stopper (20) there are provided means (21, 25, 28) that allow connection of the interior of the cylindrical body (15) to the environment during the lyophilization.

18 Claims, 8 Drawing Sheets

U.S. PATENT DOCUMENTS

| | | | |
|---|---|---|---|
| 4,929,230 A | 5/1990 | Pfleger | |
| 4,994,043 A | 2/1991 | Ysebaert | |
| 5,125,892 A | 6/1992 | Drudik | |
| 5,279,606 A | 1/1994 | Haber et al. | |
| 5,637,087 A | 6/1997 | O'neil | |
| 5,637,100 A | 6/1997 | Sudo | |
| 5,779,668 A | 7/1998 | Grabenkort | |
| 5,785,683 A | 7/1998 | Szapiro et al. | |
| 5,788,670 A * | 8/1998 | Reinhard et al. | 604/89 |
| 5,817,056 A * | 10/1998 | Tanaka et al. | 604/89 |
| 5,899,881 A | 5/1999 | Grimard | |
| 6,419,656 B1 | 7/2002 | Vetter et al. | |
| 6,440,101 B1 | 8/2002 | Grabenkort et al. | |
| 6,602,223 B2 | 8/2003 | Szapiro et al. | |
| 2002/0068910 A1 | 6/2002 | Szapiro et al. | |
| 2002/0198498 A1 | 12/2002 | Porat et al. | |
| 2003/0199816 A1 | 10/2003 | Ramming | |
| 2007/0060875 A1 | 3/2007 | Bassarab et al. | |
| 2007/0060876 A1 | 3/2007 | Bassarab et al. | |
| 2007/0060877 A1 | 3/2007 | Bassarab | |
| 2007/0129673 A1 | 6/2007 | Bassarab et al. | |
| 2009/0182301 A1 | 7/2009 | Bassarab et al. | |

FOREIGN PATENT DOCUMENTS

| | | |
|---|---|---|
| CH | 621524 | 2/1981 |
| DE | 1909794 | 2/1965 |
| DE | 1930803 | 1/1966 |
| DE | 1961166 | 6/1967 |
| DE | 1491781 | 10/1969 |
| DE | 1809892 | 6/1970 |
| DE | 1815118 | 6/1970 |
| DE | 2546495 | 4/1977 |
| DE | 3213072 | 11/1982 |
| DE | 3311525 | 10/1984 |
| DE | 3736343 | 5/1989 |
| DE | 4445969 | 3/1996 |
| EP | 097880 | 1/1984 |
| EP | 0295337 | 12/1988 |
| EP | 0718002 | 6/1996 |
| EP | 1038543 | 9/2000 |
| EP | 1145703 | 10/2001 |
| EP | 1213036 | 6/2002 |
| FR | 1167766 | 11/1958 |
| FR | 2096680 | 2/1972 |
| FR | 2285150 | 4/1976 |
| GB | 730148 | 5/1955 |
| GB | 982744 | 2/1965 |
| WO | 93/04951 | 3/1995 |
| WO | 95/32015 | 11/1995 |
| WO | 98/01174 | 1/1998 |
| WO | 01/91836 | 12/2001 |
| WO | 03/084840 | 10/2003 |
| WO | 2007020237 A1 | 2/2007 |
| WO | 2007020238 A2 | 2/2007 |
| WO | 2007020239 A1 | 2/2007 |
| WO | 2007020240 A1 | 2/2007 |

OTHER PUBLICATIONS

Office Action for co-pending, related U.S. Appl. No. 11/464,493, Jul. 3, 2008.

Office Action for co-pending, related U.S. Appl. No. 11/464,493, Dec. 9, 2009.

International Search Report for International Application PCT/EP2006/065236.

International Search Report for International Application PCT/EP2006/065238.

International Search Report for International Application PCT/EP2006/065240.

International Search Report for International Application PCT/EP2006/065241.

"Die Lyophilisierung von Arzneimittenln in Fertigspritzen" by Von H. Vetter., Pharmazeutishe-Industrie-46th-year-10-pg-1045.

U.S. Appl. No. 11/464,491.

U.S. Appl. No. 11/464,492.

U.S. Appl. No. 11/464,493.

Office Action for co-pending, related U.S. Appl. No. 11/464,493, Apr. 7, 2010.

International Preliminary Report on Patentability and Written Opinion for corresponding application PCT/EP2006/065238.

International Preliminary Report on Patentability and Written Opinion for PCT/EP2006/065238.

Office Action for co-pending, related U.S. Appl. No. 11/464,493, Aug. 7, 2009.

Abstract in English for CH621524, Bottle Closure, 1981.

Abstract in English for DE1815118, publication date Jun. 25, 1970.

Abstract in English for DE3311525, publication date Oct. 4, 1984.

Abstract in English for DE3736343, publication date May 11, 1989.

Abstract in English (AU6643994) for WO-95-032015, publication date Dec. 18, 1995.

Abstract in English (AU3186297) for WO98-001174, publication date Feb. 2, 1998.

Vetter, Von H. "Lyophilization of pharmaceuticals in prefilled syringes". Science+Technology, Pharm. Ind. 46, No. 10, 1984, p. 1045-1049 translated to English. (Vetter NPL was previously cited and considered in the German language).

* cited by examiner

Fig. 8

DUAL CHAMBER CONTAINER FOR LYOPHILIZATION, PROCESS FOR THE FILLING UP AND USE THEREOF

This application claims benefit under 119(a) of DE 10 2005 038 368, which was filed on Aug. 13, 2005, and which is incorporated herein by reference in its entirety.

BACKGROUND OF THE INVENTION

1. Field of the Invention

The present invention relates to a double chamber container which is suitable, in particular, for lyophilization, to a process for filling the double chamber container, to a process for mixing the two components contained in the double chamber container, and to the use of the container.

2. Description of the Prior Art

There are pharmaceutical compositions which in their liquid state very rapidly lose their efficacy. To enable these compositions to be used in spite of their short shelf life, specific devices and processes for lyophilization have been developed. Thus, pharmaceutical preparations which cannot be used in solution over relatively long periods may be made durable by lyophilization and possibly stored away from air. The dry substance is only dissolved again, i.e., reconstituted, immediately before use. For this purpose, two-component systems have become known for re-dissolving the lyophilizate immediately before use.

As is known, lyophilizates are also used in ready-prepared syringes with two-chamber systems—the lyophilizate and solvent being stored separately and only combined just before use. Two-chamber prepared syringes of this kind have already been described in "Die Lyophilizierung von Arzneimitteln in Fertigspritzen", H. Vetter, Die Pharmazeutische Industrie, Vol. 46, 1984, No. 10, pp. 1045-1049. Specifically, ready-prepared syringes of this kind are constructed so that each of the components is housed in its own chamber, the chambers being arranged axially behind one another and only brought into contact with one another immediately before use, so that the liquid component in one chamber can flow over to the dry component in the other chamber.

In the prior art attempts have been made to find further solutions to carry out, using double chamber systems of this type, lyophilization of the solid substance present in solution, which substance may then, or after appropriate storage prior to application, be re-dissolved, the sterility of the two components being maintained during mixing. The lyophilization of solutions in a syringe is possible only under specific conditions, the fact that during the lyophilization there is only a very small cross section for the exchange of gases being problematic. The prior art contains numerous proposals to solve these problems:

Known, for example, is a multi-chamber disposable syringe according to DE 33 11 525, in which the lyophilizate is present in the syringe cylinder, in particular in the first syringe chamber which is connected to the syringe neck and is separated from the second syringe chamber by the syringe plunger. The freeze-drying, which is designed in particular for a container having a narrow opening, is carried out via two openings, for example by means of a hollow needle which is guided through the syringe neck into the first syringe chamber and is connected to an ice condenser and a vacuum pump, a second opening, through which dried gas is introduced, being provided by the free annular space between the hollow needle and syringe neck. Two hollow needles may also be pierced through the resilient plunger body from the trailing end of the syringe cylinder in order thus to freeze-dry the liquid product in the first cylinder chamber.

The patents and patent applications described in the following paragraphs, namely U.S. Pat. No. 5,788,670, EP 0 718 002 A2, U.S. Pat. No. 4,254,768, and EP 0 295 337 B1 are incorporated herein by reference in their entireties.

U.S. Pat. No. 5,788,670 describes a double chamber syringe which may be broken down into two parts, wherein two medical components may be respectively introduced into the separate cylinders and the medicament in the lower cylinder part subjected to lyophilization, both cylinder parts then being sealed and interconnected.

Similarly, EP 0 718 002 A2 describes a two-chamber syringe having a syringe cylinder consisting of two partial cylinders. For the purposes of lyophilization, the syringe head may be provided with a closure cap having axially extending recesses which provide a connection to the environment when the cap is not completely attached. The lyophilization takes place in one partial cylinder. The weak point of a construction of this type is the connection between the two chambers which, in the event of insufficient tightness, not only provides a possible point for contamination but may also result in leakage of the liquid substance during mixing. An additional process step, which must satisfy extremely stringent requirements, for connecting both partial cylinders is required. The closure cap has the further drawback that precise adjustment must be carried out to allow the recesses in the closure cap to be outwardly connected; this is not easily possible, since the recesses are concealed by the cap, owing to the shape thereof, so the position of the recesses is not easy to establish. Connection to a recess of this type—such as may, for example, prove advantageous during the lyophilization—is also not possible. In addition, the closure must be adapted to the specific shape of a syringe head.

According to U.S. Pat. No. 4,254,768, a double chamber syringe also consists of two separate cylinders which may be joined. A vent, which may be re-closed by pushing both cylinders together and by using an elastomer ring, may be provided in the side wall of the upper cylinder. The two halves of the syringe must therefore be assembled with great precision, wherein there is a risk that if insufficient care is taken to prevent displacement of both cylinders with respect to one another, the vent will be re-exposed and the system will become unsealed and contaminated. Particularly complex measures must therefore be taken to prevent this.

Finally, EP 0 295 337 B1 describes a double chamber syringe for a solid and liquid pharmaceutical composition, wherein in the first lower chamber a toward the syringe head there is located a liquid substance which is separated via a double sided bypass and a stopper from a second upper chamber b in which a solution may be lyophilized, the wall of the chamber b having a small opening allowing the solvent to escape during the lyophilization. A drawback of this proposal is that there is a relatively small spacing between the opening and the lyophilizate solution. So, on application of vacuum, there is a risk that a portion of the solution will be extracted from the cylinder. The opening is therefore also correspondingly small, as a result of which, again, much less gas is able to escape per unit of time. A further problem is that after the lyophilization and sealing the solid is located at the top of the double chamber syringe and the liquid at the bottom (toward the mouth of the syringe), so the upper stopper is pressed onto, and will probably remain stuck to, the solid. After displacement of the stopper into the double bypass, the liquid in the lower chamber must be caused to move upward toward the solid in the upper chamber, and this is not easily possible.

For this purpose, the syringe must, for example, be repeatedly rotated or shaken in order to rinse the solid out of the upper chamber and to convey it into the lower chamber where the port for the injection needle is located. The possibility of solid residues sticking to the upper stopper cannot be ruled out, so incomplete reconstitution takes place.

The above-described drawbacks demonstrate that there is still a need for a device which is easy to handle, for the reliable storage and mixing of two-component systems, of which one component is a lyophilizate and the other a solvent/dispersing medium therefor. It should, in particular, be possible to carry out lyophilization directly in the device, and this should reduce the drawbacks of the prior art. At the same time, contamination from outside should be prevented as far as possible. In particular, the subsequent mixing should take place without removing the components from the sterile interior of the device and without external intervention into the system resulting in loss of the sterile conditions. The device should also be easy to store. In addition, a process for the simple filling of such a device should be provided. The device and the process should also be suitable for implementation on an industrial scale.

SUMMARY OF THE INVENTION

The aforementioned object is achieved by the features of claim 1. According to this, there is provided a double chamber container for separately holding and combining a solid, in particular a lyophilizate and a liquid reconstitution medium therefor. This container comprises an integral cylindrical body with a closure at each of the two ends of the body, an upper movable closure, in particular a stopper, to the side of the reconstitution medium, a movable central closure (separating stopper) to the side of the lyophilizate, and a closure at the mouth of the container (lower closure). The central closure acts as a seal between the upper chamber and the lower chamber of the container. Said container has a bypass, arranged below the separating stopper, having a length L greater than the height H of the separating stopper, wherein at the lower end in the wall of the cylindrical body or in the lower stopper there are provided means which allow at least partial connection between the interior, in particular the container partial chamber, containing the component to be lyophilized and the environment during the lyophilization.

DESCRIPTION OF THE FIGURES

The accompanying figures illustrate the present device according to the invention and the procedural teaching which is to be carried out according to the invention without restricting the invention thereto. Specifically, in the drawings.

In the figures, identical parts are denoted by identical reference numerals.

List of Reference Numerals

5 Lower end, mouth on the solid side
10 Container
15 Cylindrical body
20 Closure, stopper
20.1 Upper portion of the stopper 20
20.2 Lower portion of the stopper 20
20.1a, b Engagement part
21, 21a, 21b Openings in the stopper 20
22a, b; 22.1a, b; 22.2a, b Projections, knobs
25 Lateral opening in the container
28 Cavity
30 Chamber containing solid component
33 Lyophilization solution
35 Bypass
40 Separating stopper
50 Chamber containing liquid component
60 Closure, stopper
70 Upper end on the liquid side

DETAILED DESCRIPTION OF THE INVENTION

The aforementioned object is achieved by the features of claim 1. According to this, there is provided a double chamber container for separately holding and combining a solid, in particular a lyophilizate and a liquid reconstitution medium therefor. This container comprises an integral cylindrical body with a closure at each of the two ends of the body, an upper movable closure, in particular a stopper, to the side of the reconstitution medium, a movable central closure (separating stopper) to the side of the lyophilizate, and a closure at the mouth of the container (lower closure). The central closure acts as a seal between the upper chamber and the lower chamber of the container. Said container has a bypass, arranged below the separating stopper, having a length L greater than the height H of the separating stopper, wherein at the lower end in the wall of the cylindrical body or in the lower stopper there are provided means which allow at least partial connection between the interior, in particular the container partial chamber, containing the component to be lyophilized and the environment during the lyophilization.

The present invention therefore provides an integral container specifically adapted and designed for lyophilization and having a double chamber system. There are provided specific means with which a connection between the interior of the container and the external environment may be produced. The means are arranged in such a way that the closure stopper at the lower end of the container (referred to hereinafter simply as the "lower stopper") is able to assume two positions. In a first position of the stopper, gaseous solvent is able outwardly to escape from the cylindrical container during the lyophilization. In a second position, the lower stopper tightly seals the cylindrical body. The means according to the invention may be selected from (a) at least one opening in the wall of the cylindrical body, arranged in a defined size and/or at a defined distance from the lower end of the cylindrical body;
(b) a laterally open cavity in the base of the lower stopper and/or
(c) at least one opening running continuously within the lower stopper and extending from the base of the stopper into the side, the opening in the side of the stopper being arranged in a defined size and/or at a defined distance from the base of the stopper.

As a result of variants (a) to (c), which may be provided individually or in combination, a connection is produced between the interior of the container, which contains the solution to be lyophilized, and the external environment, so lyophilization may be carried out directly in the container. During the lyophilization, the solvent in gaseous form escapes through the opening(s) provided in the lower end of the container and/or in the lower stopper or the cavity at the base of the lower stopper. In the filled and sealed state, the container is used for storing the lyophilizate and a reconstitution medium therefor in separate chambers. Both components may be mixed immediately prior to use without having to open the container.

The invention is not restricted as to the nature of the two components, provided that the solid component is a soluble powder or a solution which is lyophilized (lyophilized liquid or dried solid substance) and the other, liquid component is a reconstitution medium therefor. A pharmaceutical composition which is already solid and is subjected to a drying process may, for example, also be used. The term "lyophilization" or "freeze-drying" refers, in the present context, to the known freezing of a liquid product, whereupon the frozen product is dried by sublimation. The reconstitution medium is a solvent or dispersing medium for the lyophilizate. By combining both components, an injectable solution may be prepared, for example, in either dissolved or dispersed form. The reconstitution medium is preferably water, but may also be some other solvent or a mixture of solvents.

The cylindrical body according to the invention is a substantially elongate hollow body with two open ends, which body is integral, i.e., was made in one piece. The "cylindrical" body need not necessarily be cylindrical in shape, although this is the most common shape. Any other geometric shape for an elongate hollow body is possible, such as angular or oval, for example, in which case the closures and separating stopper and the like must be matched to the chosen shape. The material of which the cylindrical body consists or which it contains is not particularly restricted according to the invention. The container may be selected for example from plastics materials or glass. Glass is preferred on account of its transparency and its compatibility with numerous medical formulations. The cylindrical body therefore preferably consists of glass or contains glass, as this produces the least effect on the components contained therein and the body is preferably transparent. For particular requirements, however, other materials may be suitable, such as special plastics materials or the like. Medical safety is particularly important, as it is desirable that there be as little interaction as possible with the medium contained therein.

Apart from the closure stopper (lower stopper), the double chamber container further comprises 2 closures, one of which is provided at the solid (lower) end and the other at the liquid (upper) end of the container. The movable closure means are not further restricted, provided that the closure device at the liquid end is movable by the application of force, so the separating stopper may be moved out of its position and into the bypass in order to allow both components to be mixed.

The terms "top" and "bottom" do not mean that the part of the container thus specified is always at the top or bottom; this is intended primarily as an unambiguous description. For example, the container may be inverted during the lyophilization, but the term originally used is retained for reasons of clarity.

All of the closures are preferably stoppers which provide a suitable seal, are inert with respect to the medium which is to be added and maintain the sterility of the added components. The lower closure is, for example, a rubber stopper with a flanged cap. It is also possible to provide a removable closure. If the container is a carpule, a rubber closure may be provided which can be pierced with an injection needle. However, any other closure known in the art may also be used.

In order to allow lyophilization to be carried out using the container, means are provided which allow the solvent to escape from the container. According to variant (a), at least one opening is provided in the wall of the cylindrical body in a defined size and/or at a defined distance from the lower end of the cylindrical body. The term "a defined size and/or a defined distance from the lower end" means that these parameters are selected in such a way that, in the first position which the stopper is able to assume, the opening(s) are not closed, i.e., there is at least partial connection to the external environment, whereas in a second position of the stopper the opening(s) are closed. The opening(s) at the lower end of the container are therefore positioned in such a way that they remain at least partially open on application or attachment of a stopper (first position), so during the lyophilization the solvent is able to escape from the pharmaceutical composition without difficulty, whereas the open end of the container is substantially sealed to prevent the infiltration of foreign substances. In the first position, the stopper therefore covers, according to this embodiment, only the lower end of the cylindrical container, but leaves the openings provided at least partially open. In the second position, the stopper closes both the lower end and the opening(s) in a completely sealed manner with respect to the external environment.

One, two, three, four, or more openings may, for example, be arranged at the lower end of the cylindrical body in a defined size and/or at a defined distance from the lower end of the closure. According to the invention, at least one opening may preferably be respectively arranged at opposing sides of the lower end of the container. The openings may also be arranged in pairs and/or be provided, for example, symmetrically over a portion or the entire region of the lower end.

The opening(s) may be selected from round, oval, elongate, triangular, square, or polygonal openings, in particular slots or holes, and may be arranged below one another and/or next to one another. Even an opening of this type ensures a sufficiently large cross section for the exchange of gases during the lyophilization.

According to variants (b) and (c) according to the invention, there are provided in the lower stopper means which produce a connection between the interior of the container and the external environment.

According to a preferred embodiment, the lower stopper is divided into a lower portion and an upper portion. The upper portion has a diameter D1 preferably substantially equal to or even more preferably greater than the lower portion having the diameter D2, so $D1 \geqq D2$. Suitable fluid tightness may, in particular, be achieved in this way.

The shape of the lower stopper is not particularly restricted according to the invention, provided that said stopper is suitable for tightly sealing the container and is able—as stated above—to assume the first and second positions. According to the invention, the lower stopper may have any shape known to a person skilled in the art and with which a cylindrical container may be sealed. The stopper may, for example, be symmetrical—for example, rotationally symmetrical or else mirror-symmetrical to the centre axis.

The material of the lower stopper is not particularly restricted. Preferably, a resilient, flexible material is used. Examples include rubber, caoutchouc, such as natural or synthetic rubber, plastics materials, such as elastomers, thermoplastics, thermoplastic elastomers, or similar materials. The material of the stopper may also be provided with a coating, as a result of which the tightness of the material may, for example, be improved.

In addition, the lower stopper may be provided with a further closure means such as a seal, a covering, plastics material or flanged cap, such as a metal ring, made for example from aluminum. However, this is not necessary in every case. These closure means are not particularly restricted. A removable closure means may also be provided. However, any other covering closure known to a person skilled in the art may also be used.

If the lower stopper is constructed rotationally symmetrically, it is particularly preferable if the radius R1 of the upper portion is equal to or greater than the radius R2 of the lower portion. Particularly preferably, the radius R1 of the upper portion is greater than the radius R2 of the lower portion.

According to a preferred embodiment, the length L1 of the upper portion in the direction of the longitudinal axis is equal to or less than the length L2 of the lower portion of the stopper.

Particularly preferably, the stopper has a lower portion for engagement with the cylindrical body and an upper portion for covering the cylindrical body. It is particularly expedient if the lower and upper portions of the lower stopper are adapted to the shape of the lower end of the cylindrical body, so said portions are able, in the second position of the stopper, to seal off the container in a fluid-tight and microbe-tight manner. The upper portion of the stopper may, for example, have an almost arbitrary geometric shape, such as a square, round or oval shape, provided that it performs its covering function. According to a particularly expedient configuration, the lower portion is used for engagement with the lower end of the cylindrical body, which end may, for example, be tapered in a similar manner to the neck of a bottle. However, the lower portion may also be configured in such a way that it partially, or preferably completely, encompasses the lower end of the cylindrical body.

According to variant (b) according to the invention, at least one internal, laterally open cavity in the base of the lower stopper may be configured in such a way that when said stopper is attached (first position of the lower stopper), it produces an at least partial connection between the interior of the container and the external environment. The cavity may be of any size and shape, wherein said cavity should, for the desired application, facilitate an adequate gas cross section for evaporating a solvent from a lyophilizate solution. In the first position, the lower stopper is attached to the lower end of the container in such a way that the laterally open cavity produces an at least partial connection to the environment. In the second position, the cavity is closed by pushing in the stopper. The cavity preferably extends over a determined defined part of the lower portion of the stopper. If a cavity is provided, the lower portion has engagement parts which, when the cylindrical body is sealed, extend partially, preferably completely, into said body or partially, preferably completely, encompass the lower end thereof.

The cavity may be arranged centrally in the base of the lower stopper, although this is not necessary. The cavity is preferably configured symmetrically in the base of the lower stopper, in particular in the lower portion of the stopper. The term "laterally open cavity" refers, in the context of the invention, to the fact that the cavity is not rotationally symmetrical, with only one opening in the base, but rather the opening is laterally raised and extends through the lower portion of the stopper, i.e., the cavity is open on opposing sides.

The cavity in the base of the stopper produces, at the lower end of the stopper, an engagement part which, as a closure, either engages with or encompasses the lower end of the cylindrical body. This preferred configuration according to the invention allows both material to be saved and the fit of the stopper, which advantageously has a specific resilience, to be significantly improved. This cavity in the lower stopper also increases the flexibility or pliability of the stopper, allowing the stopper to be positioned more easily. The cavity forms, in the lower portion, engagement parts which, when the cylindrical body is sealed, extend partially, preferably completely, into the lower end or partially, preferably completely, encompass said lower end.

The engagement parts particularly preferably have a greater diameter toward the upper portion than at the other end toward the container, i.e., the lower portion preferably tapers toward the base. Particularly preferably, the diameter of the lower portion decreases continuously toward the container. Particularly advantageously, the engagement parts may be spread outward in order to ensure even more reliable support in the container.

Support means in the form of one or more projections are advantageously provided on the lower stopper, preferably in the lower portion of the stopper. Said projections may be set apart from one another and optionally displaced with respect to one another on the outer or inner surface of the engagement parts of the lower stopper, depending on whether the stopper engages with or encompasses the lower end. The lower end is shaped in such a way that the projections enter into contact with the inner or outer wall of the cylindrical body in such a way that said projections improve the support of the stopper. The projections are preferably arranged at a defined distance in such a way as to support the stopper in a first position, so gaseous solvent is able to escape through the openings provided laterally in the cavity during the lyophilization. In the second position, the stopper is then pressed in and the container is then tightly sealed by the lower stopper.

The projections are, for example, provided on the outer surface of the engagement part of the stopper in order then, in engagement with the inner wall of the cylindrical body, to provide the lower stopper with sufficient support in a first position. The projections may also be provided on the inner surface of the engagement parts of the stopper, i.e., practically in the cavity itself, in order to enter into external engagement with the outer wall of the lower end of the cylindrical body and to impart sufficient support to the stopper by engagement.

The projections are not particularly restricted according to the invention; one or more knobs, beads or lips or the like may, for example, be provided. The projections are preferably arranged in pairs, even more preferably symmetrically, on the lower portion of the stopper, in particular on the engagement parts. The projections are arranged particularly preferably symmetrically, i.e., a projection on one engagement part and a projection on the other engagement part, at the same level and having the same dimensions.

According to a further preferred embodiment of the invention, one or more recesses, into which the projections fit, are provided on the inner wall or outer wall at the upper end of the cylindrical body. Said recesses may be formed, in a first and/or second position of the lower stopper, as locking means. The recesses are accordingly provided at a distance and in a size such that the projections on the lower stopper may engage with the recesses in the wall of the cylindrical body in order to provide the lower stopper with additional support in preferably both positions.

The recesses are preferably selected from one or more grooves, channels, indentations, holes or the like.

According to variant (c) of the invention, there is provided at least one opening extending from the base of the stopper into the lateral surface. This opening is arranged in a defined size and/or at a defined distance from the base in the lateral surface or side of the stopper, starting in the lateral surface of the stopper, into the interior of the stopper, and extends continuously up to the base thereof. The defined distance, in the present case: for the arrangement of the opening in the lateral surface, or the defined size as in variants (a) and (b), are selected, in such a way that, in a first position, the stopper seals the lower end of the cylindrical body without closing the opening(s) in the lateral surface of the stopper. In a second position, the opening(s) in the lateral surface of the stopper, like the lower end of the cylindrical container, are tightly sealed, so there is no longer a connection to the external environment. A combination of variants (a) and (b), or (a) and (c), or (b) and (c) is also possible.

In addition to the lower and upper stoppers, the cylindrical double chamber container also has a separating stopper in the interior of the container. The separating stopper arranged in the cylindrical body defines the size/the volume/the dimensions of the two chambers and functions as a liquid barrier device for the liquid component, which is prevented from passing into the other chamber. The shape of the separating stopper is not particularly restricted. Said stopper has a suitable three-dimensional shape, so the two chambers are mutually sealed. The separating stopper may have any suitable shape, a cylindrical shape, a cylindrical shape with rounded sides, a dumbbell shape, cuboid, conical, truncated frustum or conical shape being preferred.

On application of a force, in particular a manual application of pressure, the separating stopper should, in any case, be displaceable onto the stopper at the upper end of the chamber, and therefore onto the liquid component.

The separating stopper is preferably made from rubber, caoutchouc, such as natural or synthetic rubber, plastics materials, such as elastomers, thermoplastics, thermoplastic elastomers, and similar materials. The material of the separating stopper should ensure sealing of both chambers from one another, for example during storage.

According to a preferred embodiment according to the invention, the separating stopper has a suitable shape, size and/or material which both substantially prevents undesired displacement from its initially fixed and defined position in the cylindrical body and facilitates intentional movement of the separating stopper into the bypass. The corresponding provision of a suitable shape with (adhesive) knobs, lips, beads or the like and/or the selection of a suitable diameter may expediently provide a balanced solution. Should the frictional adhesion of the separating stopper to the wall of the cylindrical body not be sufficient for the intended application, i.e., to prevent accidental slippage or movement of the separating stopper, said stopper may preferably also be secured to the inner wall of the cylindrical body using small knobs provided on the separating stopper.

In the present invention, the term "shape" is intended to refer to the outer form or geometry. The term "size" is intended to refer to the dimensions, i.e., the ratios of magnitude.

The separating stopper preferably has an external diameter which is greater than the internal diameter of the cylindrical body, so that sufficient pressure is built up between the inner wall and shaped member to close off the interface but so that the shaped member is movable in the container under the effect of force, in particular the effect of manual force. The separating stopper is therefore arranged movably or displaceably and in a fluid-tight manner within the container.

Further provided in the cylindrical body is at least one bypass in the form of a bypass line along the cylindrical body located in the chamber of the lyophilizate. The bypass is not particularly restricted, provided that its length is greater than the height of the separating stopper, so when the stopper is pressed into the bypass, it allows the reconstitution medium to access the chamber containing the lyophilizate. In other words, the bypass is a region in the cylindrical body defining a bypass zone which, along the longitudinal axis, is longer than the length of the separating stopper along the longitudinal axis, the bypass being arranged in such a way and being of a size such that as soon as the separating stopper is pushed into the bypass zone and is then located therein, the liquid component is able to flow around the stopper. The bypass, which is arranged below the separating stopper, accordingly has a length L in the longitudinal axis which is greater than the height H of the separating stopper in the longitudinal axis. The bypass is therefore longer than the stopper, as a result of which liquid flows around the stopper when the stopper is in the "bypass" position. When the separating stopper is in the bypass zone, both ends of the bypass accordingly protrude beyond the entire length of said stopper.

The bypass may be provided with and without alteration to the internal diameter of the container, such as an extension of the internal diameter of the cylinder, i.e., a protuberance or sectional extension which extends, for example, radially outward and changes the internal diameter of the container. In the other case, the inner wall has an indentation in the longitudinal direction such as a channel or groove or change in the internal diameter of the container.

The bypass may be provided unilaterally, bilaterally or multiply, i.e., on one or more sides of the container. Preferably, it is provided only on one side of the inner wall of the container.

In the filled state for storage, the central stopper separates the chamber containing the solid from the chamber containing the liquid, the bypass being located in the region of the solid chamber and being displaced into the bypass zone for the purposes of mixing. Projections, such as (adhesive) knobs, beads, or lips are, for example, preferably provided in the bypass zone in order to secure the separating stopper in said zone and to ensure unimpeded access to the solid component for the reconstitution medium.

If the liquid is subjected to pressure, the separating stopper continues to adhere to the inner wall of the cylindrical body by frictional forces. If the frictional adhesion of the separating stopper to the wall of the cylindrical body is not sufficient for a specific application, to prevent accidental movement, said body may additionally be secured using small suitable channels, lips, or knobs to adhere to the inner wall of the cylindrical body. The pressure therefore does not increase in the other chamber. As a result, a differential pressure is produced between the two chambers. Owing to the application of pressure, the separating stopper is finally moved toward the bypass, as a result of which, as soon as the separating stopper is located completely in the bypass, the liquid component is able to flow into the other chamber and both components are mixed.

The invention also relates to a process for filling the double chamber container according to the invention, comprising the steps of:
(1) positioning a cylindrical body with the lower end facing upward;
(2) inserting a separating stopper into the cylindrical body below a bypass;
(3) filling the cylindrical body with a lyophilization solution via the open lower end of the cylindrical body;
(4) placing a stopper onto the open lower end in a first position so that the outward escape of gaseous solvent from the cylindrical body is facilitated by suitable means;
(5) lyophilizing the lyophilization solution in the lyophilizer, the gaseous solvent escaping from the cylindrical body via the means, and a lyophilizate cake being obtained;
(6) pressing the stopper into a second position and sealing the lower end of the cylindrical body and optionally the means provided for the escape of gaseous solvent;
(7) inverting the cylindrical body through 180°;
(8) filling the cylindrical body with reconstitution medium via the open upper end and
(9) sealing the upper end of the cylindrical body with a closure.

The process will hereinafter be described in detail; any individual features described in relation to the process also apply accordingly to the double chamber container and vice versa.

In a first step of the filling process according to the invention, the cylindrical container is positioned in such a way that the lower end or the mouth of the cylindrical body points upward. The lower end of the container may, for example, be tapered. Then, in step (2), a separating stopper is inserted into the cylindrical body below a bypass. Then, in step (3), the cylindrical body is filled with a lyophilization solution via the open "lower" end of the cylindrical body, which end is directed upward. This may be an arbitrary solution intended to be lyophilized—for example, a pharmaceutical composition, the shelf life of which may be extended by lyophilization.

Subsequently, in step (4), a stopper is attached to the open, upwardly directed end, in a first position, gaseous solvent being able outwardly to escape from the cylindrical body via suitable means. These suitable means are those corresponding to variants (a) to (c) according to the invention or a combination thereof.

According to variant (a), at least one opening is provided in the wall at the "lower" end of the cylindrical body. A stopper partially seals the end where the opening(s) are located in such a way that the opening(s) provided are not covered by the stopper but rather remain outwardly open, whereas the end is covered. A fundamental aspect of variant (a) of the present invention is that this separating stop is inserted only partially into the lower end of the glass body, so the solvent is able laterally to escape via the opening(s) in the cylindrical body during the lyophilization. Just one lateral opening is sufficient; a plurality of lateral openings is preferred. In variant (a), this is the first position of the stopper.

According to variant (b), at least one laterally open cavity is provided in the base of the lower stopper and, according to variant (c), there is provided at least one opening extending from the base of the lower stopper, via the interior thereof, into the lateral surface thereof.

Common to the three variants according to the invention is the fact that they allow the stopper, in a first position, to provide access to the environment, through which solvent is able to evaporate during the lyophilization, and the stopper, in a second position, tightly to seal the cylindrical container at one end and the means provided for the escape of solvent.

The size and shape of the openings or the cavity are not particularly restricted and may be selected arbitrarily and configured in accordance with the solvent to be drawn off and the volume to be removed. The geometry of any configurations may be selected arbitrarily.

The lyophilization takes place, according to step (5) of the process, in a manner known to a person skilled in the art, wherein the solvent escapes with the aid of the means provided, in particular one or more openings at the "lower" end of the container cylinder, or one or more openings, or a laterally open cavity in the stopper. The lyophilizer is a conventional commercial lyophilizer, the process parameters of which are, for example, automatically adjusted.

After the lyophilization, the cylindrical body is sealed in the lyophilizer, in process step (6), by pressing in the stopper. This pressing-in may, for example, take place in that the panels on which the cylindrical bodies are located are pushed together. Particularly preferably, the cylindrical body is sealed under vacuum, thus allowing the stopper easily to be pressed in. A specific mechanism may be configured for pressing in the stopper.

This allows the stopper to be pressed sufficiently far into the cylindrical body without producing excess pressure.

As a result of the geometry provided or selected, the opening(s)/cavity provided are tightly sealed by pressing the stopper into the container. The cylindrical body then contains the lyophilizate in one of the chambers, which is already sealed in the lyophilizer. The container may then be removed from the lyophilizer.

Subsequently, in step (7), the cylindrical body is inverted through 180°, so the chamber containing the lyophilizate is then the lower chamber.

The sealed container is then preferably conveyed to a filling system where, in step (8), the filling with reconstitution medium takes place via the open upper end of the cylindrical body, i.e., the solvent or dispersing medium is introduced into the upper chamber. After the filling of the container with reconstitution medium, i.e., a solvent or dispersing medium for the lyophilizate, the container is provided with a closure (step (9)). A stopper is preferably used as the upper closure. However, any other closure known to a person skilled in the art may also be used, providing that it is displaceable under the application of pressure. It is particularly expedient is the upper closure at the liquid end is a stopper made, for example, from a resilient and flexible material such as plastics material, rubber or rubber-like, resilient materials, such as elastomers, thermoplastics, thermoplastic elastomers, etc.

It is particularly expedient if the stoppers and/or closure members are supplied and inserted by means of a washing and sterilizing device or by means of an autoclave along sterile corridors. After the container has been sealed it is taken out of the sterile area through an airlock; finally it is labeled and packaged. It will be understood that in this process all the surfaces and equipment are designed for aseptic operation.

According to the invention, the separating stopper therefore performs a broad range of functions: it defines the double chamber system in the container, serves as the lower limit or base for the lyophilization solution, acts as a means for separating and sealing the components provided in the two chambers, as a result of which separate storage is easily possible even over relatively long periods of time. Finally, for mixing both components, the liquid component may be able to access the solid component by moving the separating stopper into the bypass, thus giving rise to the desired mixing. As a result of the fact that the separating stopper performs a large number of functions, the configuration according to the invention may lead to significantly simplified filling and handling.

The double chamber container is preferably not a syringe but rather a container for the separate storage of 2 substances, such as a double chamber carpule intended for single use or preferably for repeated application of the active ingredient.

The dimensions of the double chamber container depend on the volume of the solution to be produced; in human medicine, volumes of 10 ml are rarely exceeded, so volumes of up to about 20 ml are sufficient. In exceptional cases and for veterinary use, however, it is possible to exceed these volumes by a long way.

The invention also relates to a process for mixing a solid, in particular a lyophilizate, and a liquid reconstitution medium in a double chamber container according to the invention, comprising an integral cylindrical body with a closure at each of the two ends of the body, an upper movable closure, in particular a stopper, to the side of the reconstitution medium and a lower closure to the side of the lyophilizate, which is a stopper having a top, a base and a side, a separating stopper which can be moved by the application of pressure in the cylindrical body as a seal between the upper chamber and the lower chamber, a bypass, arranged below the separating stopper, having a length L greater than the height H of the separating stopper, wherein at the lower end in the wall of the cylindrical body or in the lower stopper there are provided means which allow partial connection of the interior of the cylindrical body to the environment during the lyophilization, comprising the steps of:
applying pressure to the movable upper closure until the separating stopper is moved into the bypass and
allowing the liquid component to overflow from the upper chamber into the lower chamber to obtain a mixture.

For mixing the two components, the upper closure or stopper is moved by application of an external force toward the separating stopper, pressure being applied simultaneously to the liquid side, thus causing the separating stopper to be pressed into the bypass, so the liquid component has access to the chamber containing the solid component. The two components may thus be mixed without compromising the sterile conditions of the double chamber container.

The upper closure is preferably a stopper, in particular a rubber stopper. The two components are particularly preferably mixed in such a way that the container is held perpendicularly, for example with the lower closure, i.e., the solid side or mouth, facing upward. However, the container may also be held with the lower closure facing downward.

The pressure on the upper closure or stopper may be applied using the fingers or an arbitrary punch. Both the reconstitution medium and the separating stopper then move toward the bypass. The separating stopper reaches the "bypass" position and therefore no longer performs a sealing function. The pressure exerted on the liquid component by the stopper allows the liquid to flow around the separating stopper, through the passage, opened by the bypass, between the upper and lower chambers, and to enter the chamber containing the lyophilizate.

The reconstitution medium combines with the lyophilizate and the latter is dissolved. It is entirely possible for the stopper at the upper end to be thrust up to the separating stopper. Finally, the solution is completely reconstituted and ready for use.

The invention further relates to the use of the container according to the invention in human and veterinary medicine.

The invention therefore provides a double chamber container comprising a lyophilizate and a reconstitution solution. The container according to the invention allows a substance which is unstable in solution to be freeze-dried directly in the lyophilizer and a double chamber system then to be provided in the single chamber container. The construction according to the invention therefore allows optimal storage of the two-component system without premature mixing, and therefore a loss in the efficacy of the components, taking place. The two-component system provided according to the invention may be stored in a sterilized and pre-filled state ready for use. The two components are mixed after storage, immediately prior to use. The double chamber container is suitable for single or preferably repeated application of the active ingredient.

The double chamber container allows the desired solution to be prepared immediately prior to use, simple preparation and filling, as well as speed and reliability, being possible. This is an all-in-one solution, i.e., there is provided a container comprising two chambers separated from one another by a stopper.

The double chamber container of the invention allows reconstitution of a lyophilizate in a closed two-chamber system to be carried out by taking simple measures without the imperviousness of the overall system to undesired microbial, chemical or physical external influences being cancelled out for the purposes of mixing.

The above-described double chamber system allows the container to be tightly sealed when it is still in the lyophilizer. Contamination of the lyophilizate, in particular by particles, germs and any foreign substances, is advantageously prevented as a result. In particular, contamination as may occur in an aseptic clean room, such as the entry of particles, microbes and the like, is also prevented. The entry of ambient moisture and oxygen into the lyophilizate, which can significantly impair the quality of sensitive substances, is further prevented; a gassing device downstream of the lyophilizer, for example, may therefore be dispensed with. The container may be used as primary packaging and stored clearly labeled. The use of two-component systems, in particular lyophilized preparations, may thus be simplified. The container is not restricted in any way, so it may, for example, be used in what are known as "pen systems," which are already commercially available.

The inventive achievement further consists in the use of a specific container which is designed in such a way that specific openings at one end of the container and/or the provision of a specific stopper having openings/a laterally open cavity allow lyophilization to be carried out via the end of the container and the container to be sealed while it is still in the lyophilizer.

The following description discusses a large number of variations and suggests a range of possible modifications which will be immediately apparent to a person skilled in the art.

Figure 1:
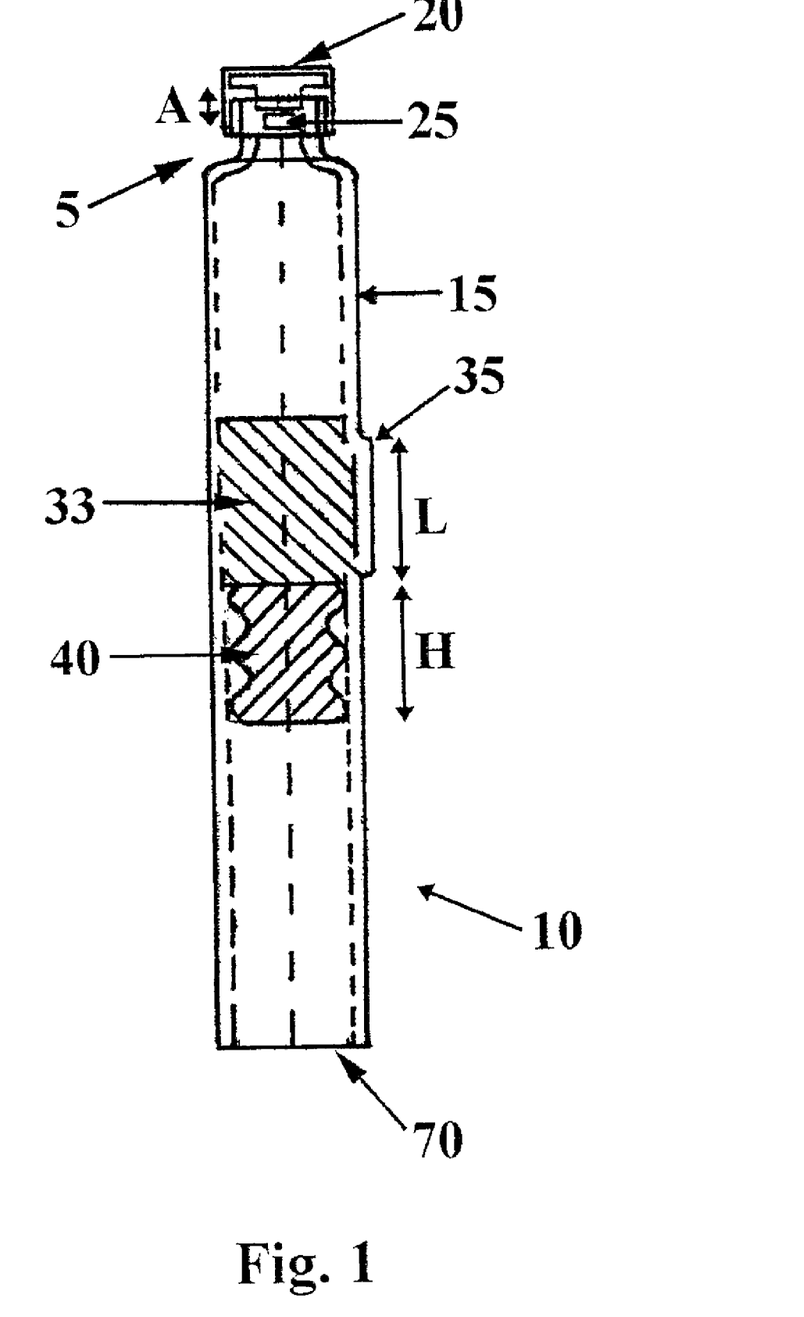
FIG. 1 is a schematic view of a container according to the invention having a lateral opening according to variant (a) prior to or during lyophilization.
Figure 2:
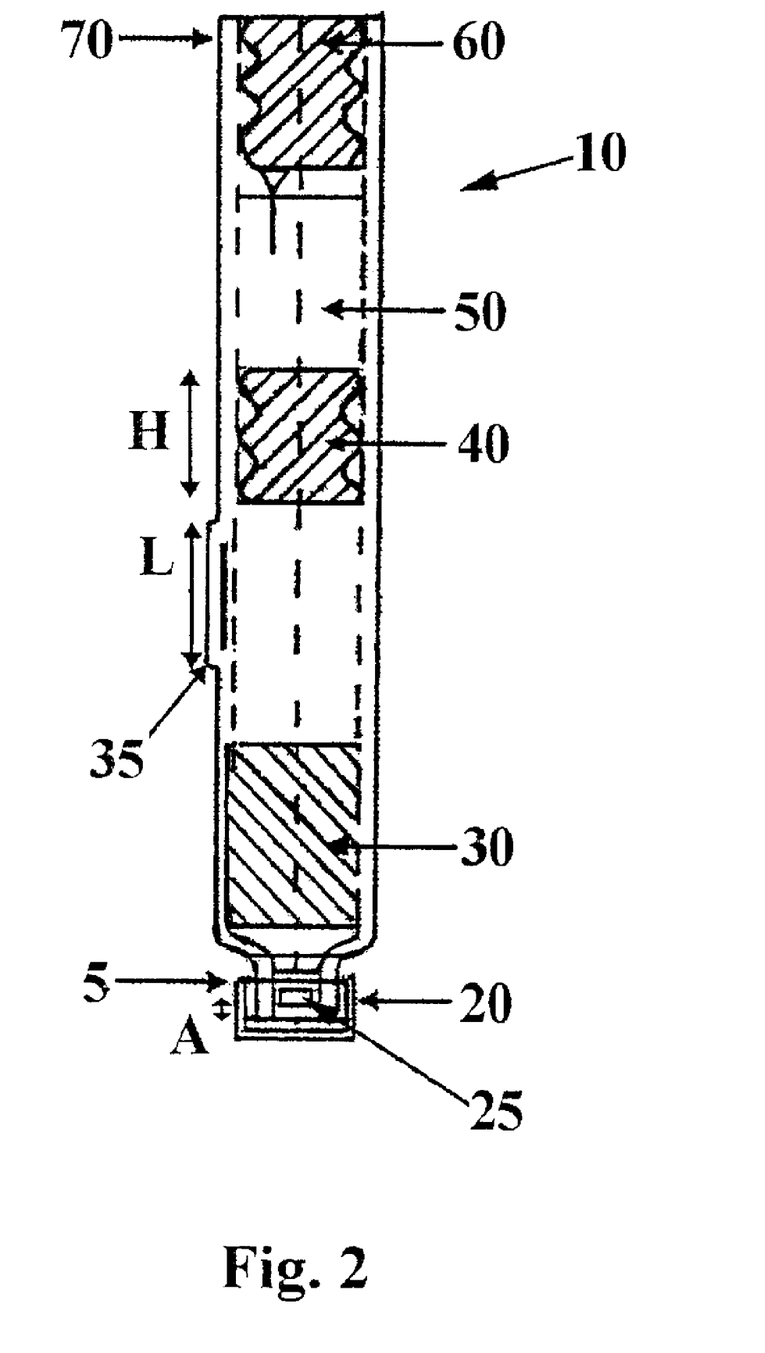
FIG. 2 is a schematic illustration of a container of the invention according to variant (a) in the filled and sealed state.

FIGS. 1 and 2 are schematic views of a container 10 of the invention according to variant (a) having a lateral opening 25, the lower stopper 20 (arranged at the top in FIG. 1) being in the first position, i.e., in the partially sealed state immediately prior to or during the carrying-out of lyophilization (FIG. 1). In FIG. 2, the stopper 20 is shown in the second position, i.e., the container has been filled and sealed, i.e., filled with lyophilizate and reconstitution medium, and may be stored for an appropriate period of time.

Specifically, FIG. 1 shows a cylindrical body 15 which may, for example, be made from glass or plastics material. Said body is provided with a separating stopper 40 below the bypass 35. A solution 33 to be lyophilized has already been introduced into the cylindrical body 15 via the open end 5 of the cylindrical body 15. This may be an arbitrary solution intended to be lyophilized—for example, a pharmaceutical composition, the shelf life of which may be extended by lyophilization.

Also provided in the cylindrical body 15 is a bypass 35, the length L of which (along the vertical axis) is greater than the height H of the separating stopper 40 (along the vertical axis). At the lower end 5, which is at the top in FIG. 1, a stopper 20 is inserted into the open end 5 in such a way that a lateral opening 25 at the end 5 of the container 10 remains outwardly open (first position of the stopper 20). In FIG. 1, the opening 25 is illustrated as a slot. Any opening of arbitrary shape which allows the solvent to leave the container during the lyophilization may, of course, be provided. The opening 25 is provided at a defined distance A (indicated by the double-headed arrow in FIG. 1) from the lower end 5 of the cylindrical body 15, so the stopper 20 seals the lower end 5 but does not close the opening 25 (first position).

The lyophilization is then carried out in a conventional manner in the lyophilizer, wherein the solvent evaporates from the lyophilization solution through the opening 25. After the lyophilization, sealing takes place in the lyophilizer by pressing in the stopper 20 at the end 5. In other words, while still in the lyophilizer, the stopper 20 is pressed down in such a way that the container is tightly sealed at this end 5. This may, for example, take place in that the panels on which the containers are located in the lyophilizer are pushed together. The container 10 may be sealed under vacuum, so it is possible to press the stopper 20 into the cylindrical body without creating excess pressure. The containers 10 are then removed from the lyophilizer. Subsequently, following inversion of the container through 180°, filling with reconstitution medium 50 takes place via the upper end 70, which is at the top in the container shown in FIG. 2. Finally, the container 10 is sealed with a closure 60, such as an end stopper (see FIG. 2).

If pressure is applied to the closure or end stopper 60, it moves toward the separating stopper 40. The separating stopper 40, which separates the chamber 50 containing the liquid component of the two-chamber system from the chamber 30 containing the solid component, is preferably configured, at its side producing a seal with respect to the wall of the cylindrical body 15, as a conventional separating stopper. Should the frictional adhesion of the separating stopper 40 to the wall of the cylindrical body 15 not be sufficient for the intended application, i.e., to prevent accidental slippage or movement of the separating stopper 40, said stopper may preferably also be secured to the inner wall of the cylindrical body 15 using small knobs.

Finally, on the further application of pressure, the separating stopper 40 moves up to the bypass 35, thus allowing the liquid component to access the chamber 30. The reconstitution of a lyophilizate takes place in this way.

Figure 8:
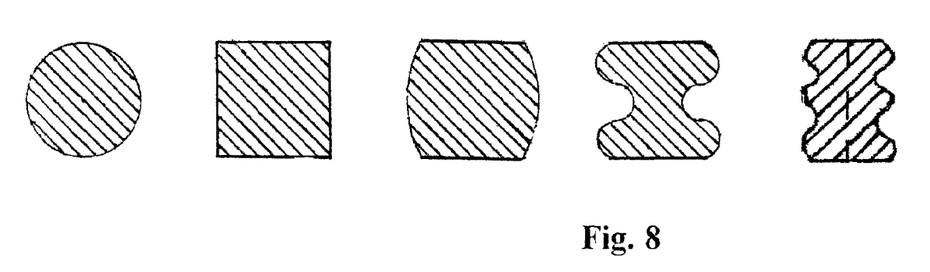
FIG. 8 is a schematic view of various forms of the separating stopper or other stopper which may be used according to the invention.

The separating stopper 40 may be of any suitable shape and size, provided that it is movable. It may, for example, as illustrated in FIG. 8, have various protrusions in the form of knobs. However, said separating stopper may also be constructed as a cylinder or as a cylinder with a ball-shaped exterior or in the form of dumbbells with two sealing surfaces, as illustrated by way of example in FIG. 8.

Figure 3A:
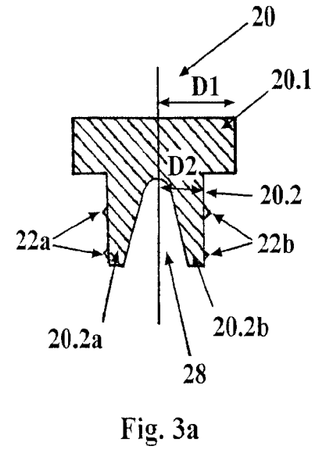
FIG. 3a is a sectional view through a stopper according to variant (b) which may be used according to the invention.
Figure 3B:
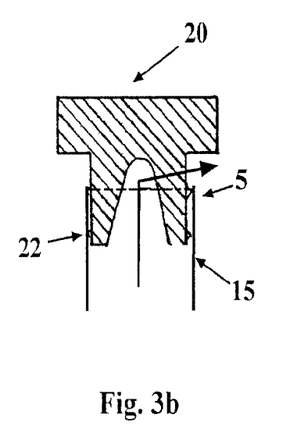
FIG. 3b is a schematic sectional view of a stopper according to FIG. 3a in the first position in the container according to the invention.
Figure 3C:
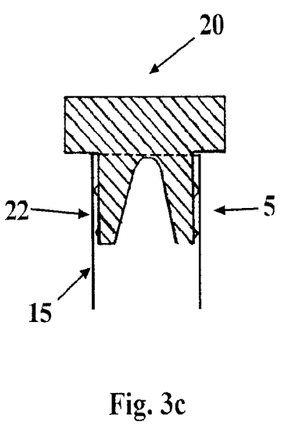
FIG. 3c is a schematic sectional view of a stopper according to FIG. 3a in the second position in the container according to the invention.
Figure 4A:
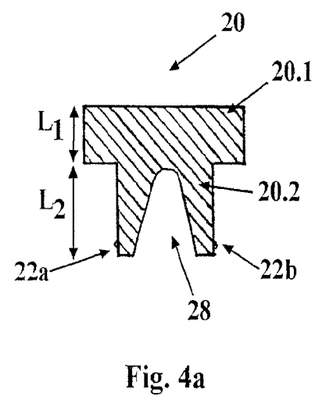
FIG. 4a is a sectional view through a stopper according to variant (b) which may be used according to the invention.
Figure 4B:
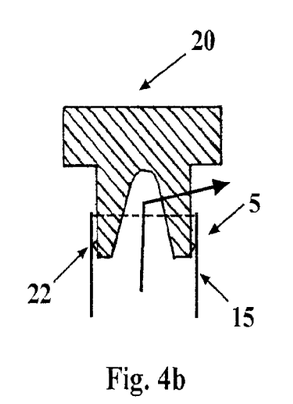
FIG. 4b is a schematic sectional view of a stopper according to FIG. 4a in the first position in the container according to the invention.
Figure 4C:
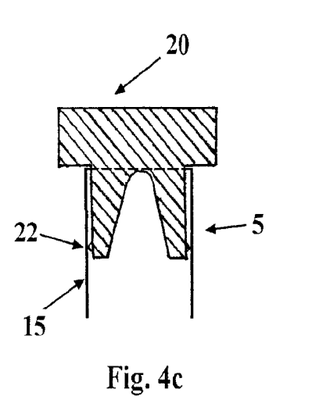
FIG. 4c is a schematic sectional view of a stopper according to FIG. 4a in the second position in the container according to the invention.
Figure 5A:
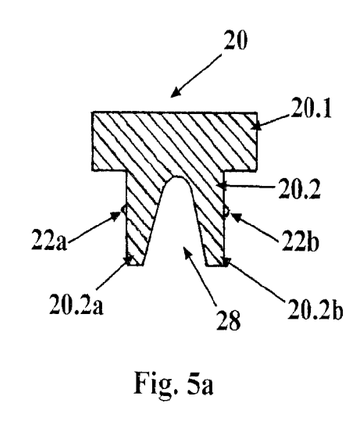
FIG. 5a is a sectional view through a stopper according to variant (b) which may be used according to the invention.

FIGS. 3a, 4a, and 5a are each schematic sectional views of a stopper 20 of the invention according to variant (b). FIG. 3a shows a stopper 20 having a lower portion 20.2 for engagement with the lower end 5 of the container and an upper portion 20.1 for covering the lower end 5 of the container. The stopper 20 is mirror-symmetrical to the centre axis. The diameter D1 of the upper portion 20.1 is preferably greater than the diameter of the lower portion D2. Moreover, in the illustrated stopper 20, the length L1 of the upper portion 20.1 is preferably less than the length L2 of the lower portion 20.2.

Also shown is a cavity 28 which is preferably arranged centrally in the base of the stopper 20 and divides the lower portion 20.1 into engagement parts 20.2a and 20.2b. In the present case, this cavity 28 is symmetrical, although this is not crucial. This allows material to be saved, the engagement with the cylindrical container 10 to be improved and, at the same time, the fit of the stopper 20, which advantageously has a specific resilience, to be significantly improved. This cavity 28 in the lower stopper 20 may also increase the flexibility or pliability of the stopper 20, allowing the stopper to be positioned even more easily. The engagement parts 20.2a, b formed by the cavity 28 in the lower portion 20.2 extend, preferably completely, into the cylindrical body 15 when said body is sealed. If the cylindrical container has, at its lower end, a narrowing of defined dimensions (taper), the engagement part of the stopper has preferably the same or slightly larger dimensions in order tightly to seal the end.

In FIGS. 3a, 4a and 5a, support means in the form of projections 22, which may, for example, be configured as knobs, lips, beads or the like, are provided on the outside of the engagement parts 20.2a and 20.2b, which form the lower portion 20.2. The projections 22 are spaced apart from one another and may optionally be displaced with respect to one another. These projections preferably correspond to indentations, recesses, grooves and the like in the mouth region of the container.

FIG. 3a shows a stopper 20 according to the invention having an upper portion 20.1 and lower engagement parts 20.2a and 20.2b each having two projections 22a and 22b each arranged in pairs and symmetrically on the outer surfaces of the engagement parts 20.2a and 20.2b. The projections 22a and 22b are arranged at a defined distance from the base of the stopper 20, so, in a first position, the laterally open cavity 28 protrudes beyond the lower end 5 of the container, thus producing a connection to the environment.

FIGS. 4a and 5a show a stopper 20 according to the invention having a respective projection 22a and 22b on each of the two engagement parts 20.2a and 20.2b which, in the illustrated case, are arranged symmetrically at the bottom or centrally in the lower portions 20.2a and 20.2b of the stopper 20. In the case of the illustrated stoppers 20 according to the invention, the diameter D1 of the upper portion 20.1 is particularly preferably greater than the diameter D2 of the lower portion 20.2, as illustrated in FIGS. 3a, 4a and 5a. In the particularly preferred illustrated embodiments, the length L1 of the upper portion 20.1 of the stopper 20 is less than the length L2 of the lower portion 20.2 of the stopper 20.

The projections 22 do not have to be provided symmetrically on the surface of the lower portion 20.2 or engagement parts 20.2a and 20.2b, although this is preferred. Any other constellations are, however, also possible. The number of the projections is not particularly restricted. The dimensions are determined on a case-by-case basis, i.e., depending on the size of the container, the shape and size of the stopper, and further factors known to a person skilled in the art.

Figure 5B:
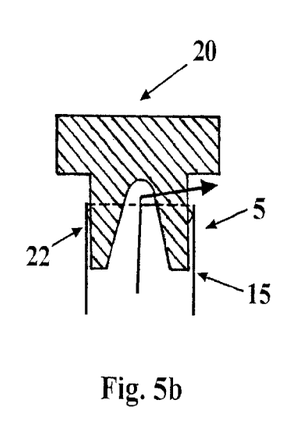
FIG. 5b is a schematic sectional view of a stopper according to FIG. 5a in the first position in the container according to the invention.
Figure 5C:
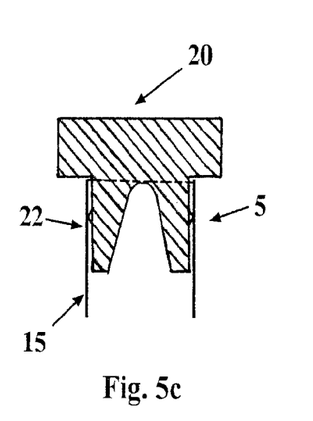
FIG. 5c is a schematic sectional view of a stopper according to FIG. 5a in the second position in the container according to the invention.

FIGS. 3b and 3c, 4b and 4c and also 5b and 5c each illustrate one of the stoppers 20 according to FIGS. 3a, 4a, and 5a in first and second positions according to the invention on the container 10 according to the invention. In the first position, the stopper 20 allows solvent to escape from the cylindrical container 10 (FIGS. 3b, 4b and 5b), the projections 22, in the present case knobs, providing the stopper with better support in the first position. The solvent is able to escape, during the lyophilization, from the laterally open cavity 28, which is not pressed completely into the glass body 15 (first position). In the second position, the stopper 20 tightly seals the lower end 5 of the container and the means provided for the escape of solvent (see FIGS. 3c, 4c and 5c). The horizontal and vertical surfaces of the stopper 20 accordingly seal the mouth or the lower end 5 of the cylindrical body 15. The knobs 22 attached to the stopper 20 do not affect the tightness but rather provide the stopper with additional support. In addition, further closure means for the lower stopper 20, such as for example a flanged cap or plastics material cap, may optionally be provided, although this is not generally necessary.

Figure 6:
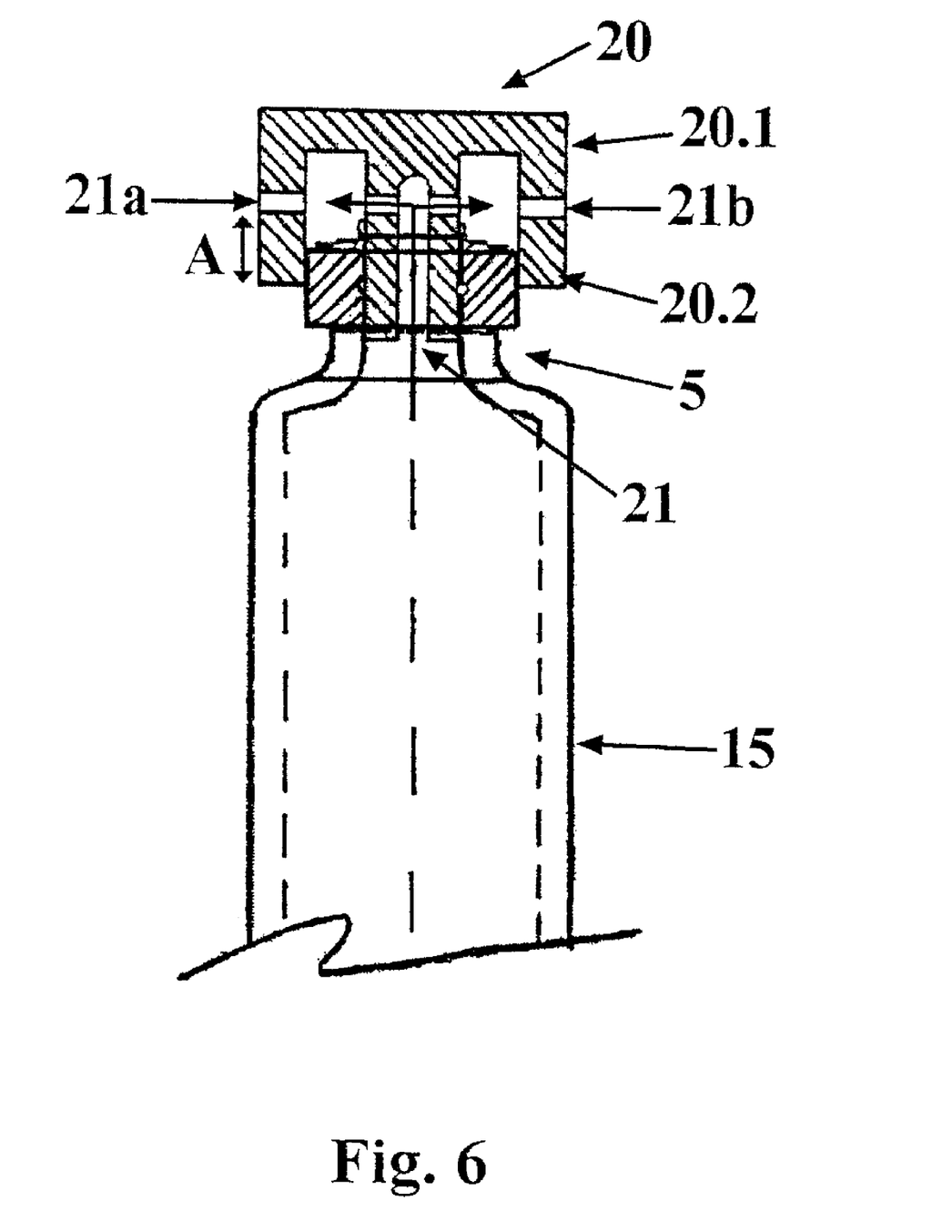
FIG. 6 is a schematic view of a detail of a container of the invention according to variant (c), the stopper being in the first position.

FIG. 6 schematically illustrates a stopper 20 according to variant (c) in a first position on a detail of a container according to the invention. The cylindrical body 15 is made, for example, from glass or plastics material and is provided at one end 5 with a stopper 20. A lyophilization solution is introduced into the cylindrical body 15 via the open upper end 5 of the cylindrical body 15 (not shown). This may be an arbitrary solution intended to be lyophilized—for example, a pharmaceutical composition, the shelf life of which may be extended by lyophilization.

The stopper 20 is inserted into the open end 5 in such a way that an opening 21 in the stopper 20 forms a connection between the interior of the container 10 and the external environment. Any opening of arbitrary shape allowing the gaseous solvent to leave the container 10 during the lyophilization may, of course, be provided. The stopper in FIG. 6 is symmetrical about a centre axis and has, in the interior of the stopper 20, a preferably centrally arranged opening 21 which extends from the base into the interior of the stopper, where it merges with two openings 21a and 21b extending in opposing directions to the lateral surface or side of the stopper 20. In the embodiment shown in the present case, the openings, for example in the form of bores, in the stopper 20 protrude into the opening in the cylindrical body 15 and outwardly encompass the mouth or the lower end 5.

Lyophilization is then carried out in a conventional manner in the lyophilizer (not shown), wherein the solvent evaporates from the lyophilization solution through the opening 21. After the lyophilization, sealing takes place in the lyophilizer by pressing the stopper 20 into the end 5, i.e., sealing takes place while still in the lyophilizer. This may take place, for example, in that the panels on which the containers are located are pushed together. The container 10 may be sealed under vacuum, so excess pressure is not produced in the already sealed chamber. As a result of the pressing of the stopper 20 into the cylindrical body 10, the openings 21a and 21b, illustrated in FIG. 6, in the stopper 20 are closed by the walls of the container (second position of the stopper 20, not shown), so the sealing function of the stopper is not compromised by the openings 21a and 21b.

The containers 10 are then removed from the lyophilizer and inverted through 180°. The filling with reconstitution medium then takes place via the open end 70. Finally, the container 10 is sealed with a closure 60, such as a stopper.

Figure 7:
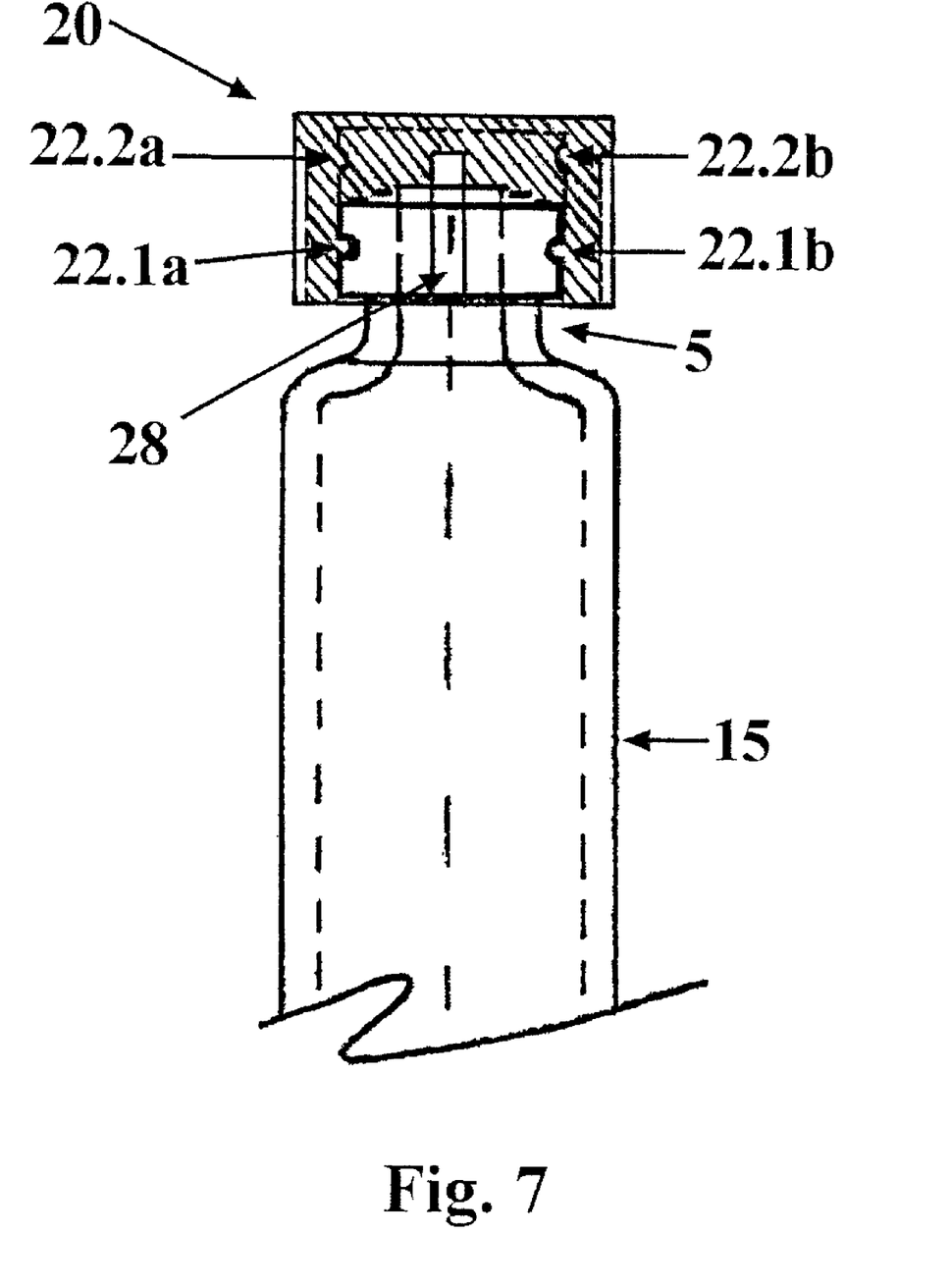
FIG. 7 is a schematic view of a detail of a container of the invention according to variant (b), the stopper being in the first position.

FIG. 7 shows a further stopper variant (variant b), illustrated in the first position. In this case, the stopper 20 encompasses the lower end or the mouth 5 only externally. Two respective knobs 22, i.e., knobs 22.1a and b and 22.2a and b, are provided on opposing sides of the stopper 20. A laterally open cavity 28 is formed in the base of the stopper 20. In the open state (first position), lower knobs 22.1a and 22.1b of the stopper 20 engage with a groove at the lower end 5 of the cylindrical body 15. The solvent is thus able to escape through the opening, directly via the open end 5. If the stopper 20 is pressed downward, the upper knobs 22.2a and 22.2b engage, in this preferred embodiment of the invention, with the groove in the bottleneck-shaped lower end 5 of the stopper 20, and the cylindrical body 15 is hermetically sealed. The lower knobs may accordingly engage with a further groove in the lower end 5 and also provide additional support by engagement below the lower end 5.

The foregoing description of the figures serves to illustrate the apparatus according to the invention and the process according to the invention. This is intended purely as a possible procedure described by way of example without restricting the invention to its contents.

What is claimed is:

1. A double chamber container for separately holding and combining a solid, in particular a lyophilizate, and a liquid reconstitution medium therefor, comprising:
    an integral cylindrical body oriented in a longitudinal direction and having opposing upper and lower ends,
    an upper movable stopper at the upper end of the cylindrical body on a side of the reconstitution medium,
    a lower movable stopper at the lower end of the cylindrical body on a side of the lyophilizate, the lower movable stopper being movable between: (i) a second position sealing the lower end of the cylindrical body; and (ii) a first position permitting at least partial connection of an interior of the cylindrical body to an exterior environment during the lyophilization, wherein the lower movable stopper includes first, second, and third opening sections, the first opening section extending in the longitudinal direction from the interior of the cylindrical body through the lower end thereof to a junction of the second and third opening sections, and the second and third opening sections extending in opposite directions from the junction to the exterior environment,
    a separating stopper which can be moved by an application of pressure in the cylindrical body as a seal between an upper chamber and a lower chamber, and
    a bypass, arranged below the separating stopper, having a length L greater than a height H of the separating stopper.

2. The double chamber container according to claim 1, wherein the lower movable stopper has a lower portion for engagement with the lower end of the cylindrical body and an upper portion for covering the cylindrical body.

3. The double chamber container according to claim 2, wherein the lower portion and the upper portion of the lower movable stopper are adapted to a shape of the lower end of the cylindrical body in order to seal off said body in a fluid-tight manner in the second position of the lower movable stopper.

4. The double chamber container according to claim 2, wherein the upper portion has a diameter D1 equal to or greater than the lower portion having the diameter D2, so D1≧D2.

5. The double chamber container according to claim 2, wherein the first, second, and third opening sections are disposed in the lower portion such that respective ends of the second and third opening sections, opposite of the junction operate to: (i) freely communicate with the exterior environment when the lower movable stopper is in the first position; and (ii) seal against the cylindrical body near the lower end thereof when the lower movable stopper is in the second position.

6. The double chamber container according to claim 2, wherein the lower movable stopper has support means in a form of one or more projections which, either on an inner or a outer wall of the lower end of the cylindrical body, improve the support of the lower movable stopper in the first or second position.

7. The double chamber container according to claim 6, wherein recesses, with which the projections engage, are provided on the inner wall or the outer wall at the upper end of the cylindrical body.

8. The double chamber container according to claim 1, wherein the lyophilizate is a pharmaceutical composition.

9. The double chamber container according to claim 1, wherein the reconstitution medium is a solvent or dispersing medium for the lyophilizate.

10. A process for filling the double chamber container according to claim 1, comprising the steps of:
(1) positioning the cylindrical body with the lower end facing upward;
(2) inserting the separating stopper into the cylindrical body below the bypass;
(3) filling the cylindrical body with a lyophilization solution via the open lower end of the cylindrical body;
(4) placing the lower movable stopper onto the open lower end in the first position so that the outward escape of gaseous solvent from the cylindrical body is facilitated by the first, second, and third opening sections;
(5) lyophilizing the lyophilization solution in a lyophilizer, the gaseous solvent escaping from the cylindrical body via the first, second, and third opening sections, and a lyophilizate cake being obtained;
(6) pressing the lower movable stopper into a second position and sealing the lower end of the cylindrical body and prohibiting the escape of gaseous solvent through the first, second, and third opening sections;
(7) inverting the cylindrical body through 180°;
(8) filling the cylindrical body with reconstitution medium via the open upper end; and
(9) sealing the upper end of the cylindrical body with a closure.

11. The process according to claim 10, wherein the pressing-in of the lower movable stopper according to step (6) is carried out in the lyophilizer.

12. The process according to claim 11, wherein the pressing-in of the lower movable stopper is carried out by pushing together panels on which the cylindrical bodies are located.

13. The process according to claim 10, wherein the pressing-in of the lower movable stopper according to step (6) is carried out under vacuum.

14. A process for mixing a solid, in particular a lyophilizate, and a liquid reconstitution medium therefor, in a double chamber container according to claim 1, comprising the steps of:
applying pressure to the upper movable upper stopper until the separating stopper is moved into the bypass; and
allowing the liquid component to overflow from the upper chamber into the lower chamber to obtain a mixture.

15. The process according to claim 14, wherein during the mixing process the cylindrical body is held perpendicularly with the lower movable stopper facing upward.

16. The process according to claim 14, wherein the pressure is applied to the movable upper stopper using a punch.

17. The process according to claim 14, wherein the upper movable stopper is thrust up to the separating stopper.

18. A double chamber container for separately holding and combining a solid, in particular a lyophilizate, and a liquid reconstitution medium therefor, comprising:
an integral cylindrical body oriented in a longitudinal direction and having opposing upper and lower ends, the lower end including a laterally directed opening through a wall of the cylindrical body from an interior to an exterior thereof,
an upper movable stopper at the upper end of the cylindrical body on a side of the reconstitution medium,
a lower movable stopper at the lower end of the cylindrical body on a side of the lyophilizate, the lower movable stopper being movable between: (i) a second position sealing the laterally directed opening through the cylindrical body; and (ii) a first position permitting at least partial connection of the interior of the cylindrical body to an exterior environment through the laterally directed opening,
a separating stopper which can be moved by an application of pressure in the cylindrical body as a seal between an upper chamber and a lower chamber, and
a bypass, arranged below the separating stopper, having a length L greater than a height H of the separating stopper.

* * * * *